United States Patent [19]

Harrod

[11] Patent Number: 4,526,303

[45] Date of Patent: Jul. 2, 1985

[54] SYRINGES

[75] Inventor: Christopher G. C. Harrod, Surrey, England

[73] Assignee: Dentsply Research & Development Corp., Milford, Del.

[21] Appl. No.: 545,813

[22] Filed: Oct. 26, 1983

[30] Foreign Application Priority Data

Nov. 5, 1982 [GB] United Kingdom ............... 8231600

[51] Int. Cl.³ ............................................. B67D 5/46
[52] U.S. Cl. ................................. 222/386.5; 222/386; 222/391
[58] Field of Search ............... 222/386, 386.5, 390, 222/391

[56] References Cited

U.S. PATENT DOCUMENTS

| | | |
|---|---|---|
| 1,612,996 | 1/1927 | Waagbo . |
| 1,976,253 | 10/1934 | Clark . |
| 2,111,582 | 3/1938 | Crewe . |
| 2,376,662 | 5/1945 | Cohen . |
| 2,778,541 | 1/1957 | Sherbondy .................... 222/391 X |
| 2,821,332 | 1/1958 | Sherbondy . |
| 3,381,861 | 5/1968 | Stein ............................. 222/391 X |
| 3,389,838 | 6/1968 | Morra et al. ................... 222/391 X |
| 4,030,643 | 6/1977 | Van Manen ........................ 222/386 |

FOREIGN PATENT DOCUMENTS 709563  8/1941  Fed. Rep. of Germany ...... 222/386

Primary Examiner—Charles A. Marmor
Attorney, Agent, or Firm—C. Hercus Just; Edward J. Hanson, Jr.

[57] ABSTRACT

A syringe comprises a body member detachably secured onto one end of a syringe barrel provided at its other end with a delivery tube and containing a movable piston member; a piston actuating assembly movably mounted in the body member and comprising a tube generally coaxial with the barrel and a rod movably mounted within the tube; and a pawl for moving said piston actuating assembly whereby the tube is first displaced to move the piston to the distal end of the barrel and the rod is then moved to pierce the central region of the piston member and to pass through the piston into the delivery tube.

3 Claims, 3 Drawing Figures

SYRINGES

BACKGROUND OF THE INVENTION

This invention is concerned with improvements in and relating to syringes, particularly to syringes for use in medicine for applying more or less viscous materials, such as bone cements, to a desired site.

Basically, such a syringe comprises a barrel for containing material to be dispensed, a delivery tube or nozzle attached to one end of the barrel, a piston movably mounted in the barrel for forcing material contained in the barrel from the barrel to and through the delivery tube, and means for actuating the piston. Such syringes may have a disposable barrel, piston, and delivery tube since it is thereby possible to provide these elements of the syringe, which come into contact with the material to be dispensed in a pre-sterilized form. It is with this form of syringe that the present invention is concerned.

One problem which is encountered with conventional syringes of this type is that not all the material placed into the syringe is dispensed, since after the piston has been moved the length of the barrel, an appreciable amount of material may remain in the delivery tube which is commonly of some length, for example from 3 to 6 inches (7.5–15 cms).

SUMMARY OF THE INVENTION

According to the invention, there is provided a syringe comprising a body member detachably secured to one end of a syringe barrel provided at its other end with a delivery tube and containing a movable piston member; a piston actuating assembly movably mounted in the body member and comprising a tube generally coaxial with the barrel, a rod movably mounted with the tube, and means for moving said piston actuating assembly, whereby the said tube is first displaced to move the piston to the distal end of the barrel and the said rod is then moved to pierce the central region of the piston member and to pass through the piston into the delivery tube.

The body member of the syringe will be generally provided with a handle extending laterally of the barrel/piston actuating assembly axis and the means for moving the piston actuating assembly is conveniently operated by means of a pivoted lever arranged so that it may be moved by squeezing or pulling the lever towards the handle. The tube member of the piston actuating assembly is conveniently moved by means of a rack and pawl arrangement, the end tube being provided with suitable grooves to form the rack. Similarly, the means for moving the rod in the piston actuating assembly may conveniently take the form of a rack and pawl arrangement.

In the syringe of the invention, the barrel is conveniently connected to the delivery tube by means of an end cap detachably secured to the distal end of the barrel and to which the delivery tube is also detachably secured.

As noted above, the barrel, piston delivery tube, and end-cap, when present, are of a disposable nature, to enable them to be presented in a pre-sterilized form. The rod in the piston actuating means may, in accordance with one embodiment of the invention, also be disposable and, in another embodiment of the invention, is a reusable item.

In order that the invention may be well understood, reference will now be made to the accompanying drawings in which:

DETAILED DESCRIPTION OF THE PREFERRED EMBODIMENT OF THE INVENTION

Figure 1:
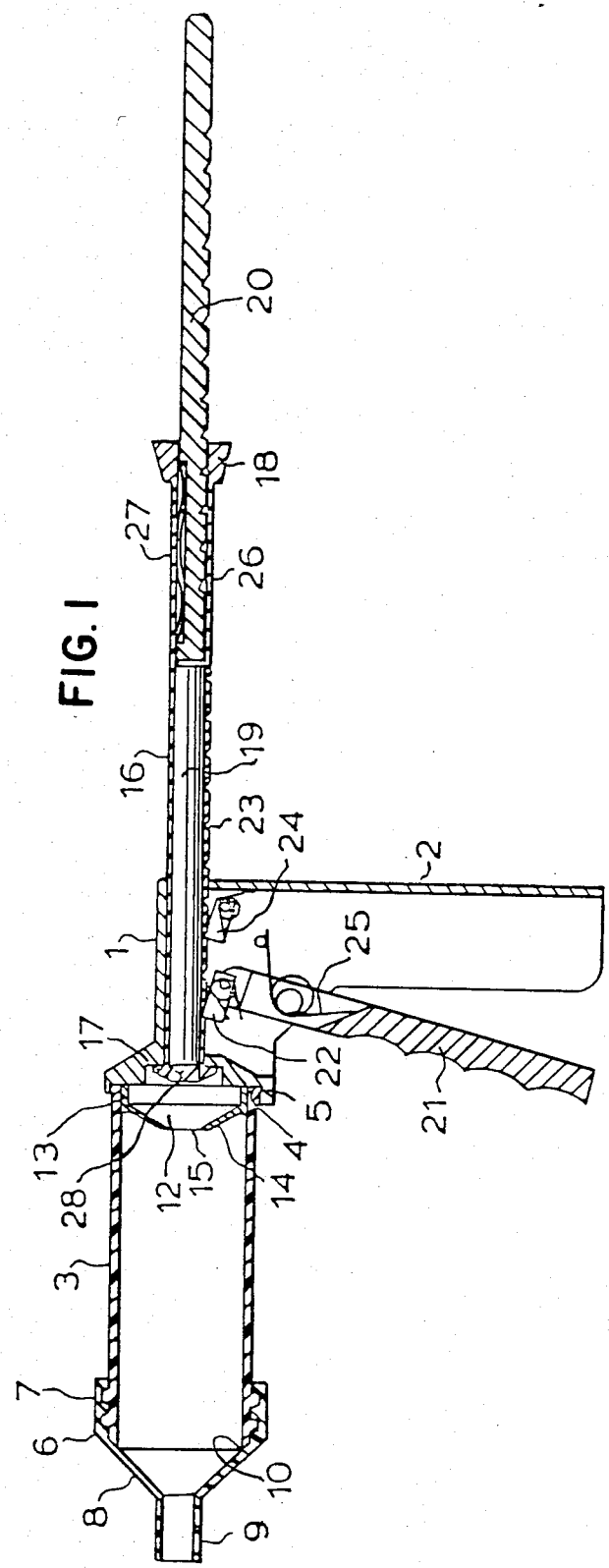
FIG. 1 is a longitudinal section through one embodiment of a syringe in accordance with the invention with the delivery tube omitted.
Figure 2:
FIG. 2 is a longitudinal section through a delivery tube for use with the syringe shown in FIG. 1.

As shown in FIG. 1 of the drawings, a syringe in accordance with the invention comprises a body member 1 having an integrally formed handle 2. A syringe barrel 3 is detachably secured to body member 1 by a snap fit between an external annular ring 4 formed at the proximal end of barrel 3 engaging in an annular recess 5 in the forward end which is the left-hand end, as shown in the drawing, of body member 1. As discussed below, barrel member 3 is conveniently formed of plastics material and is disposable. An end cap 6 is removably secured to the distal end of the barrel 3. End cap 6 comprises a cylindrical portion 7 connected via a truncated conical portion 8 to a nozzle member 9 and is detachably secured to barrel 3 by means of cooperating screw threads on the outside of the distal end of barrel 3 and the inside of cylindrical portion 7 of end cap 6. Preferably the cooperating threads are of the quick acting, rapidly translating type. In order to provide for an improved seal between end cap 6 and barrel 3 the latter is provided, at its distal end, with a deformable annular lip 10. A similar sealing effect may be obtained by employing a separate sealing ring, such as an O-ring, or by providing an appropriately located sealing lip on the inner surface of end cap 6. A delivery tube 11, see FIG. 2, is push-fitted over the outside of delivery nozzle 6 to complete the assembly. A piston 12 is mounted within barrel 3 and, as shown in the drawings, comprises an annular collar 13 integrally formed with truncated conical web 14 the central portion 15 of which is weakened in comparison with the remainder of the web, i.e. is of reduced thickness. The piston may take other forms, e.g. may be generally flat, but it is generally desirable that it be provided with a centrally weakened portion.

Mounted within body member 1 is an assembly for actuating piston 12 and comprising a tubular member 16 having a head 17 for engagement with the rearward facing wall of web 14 of piston 12 and, at its other end, a stop member 18. Mounted within tube 16 are displacement bar 19 and, rearwardly thereof, actuating rod 20. An actuating lever 21 is pivotably mounted within body member 1 and is provided at its upper end with a spring loaded pawl 22 adapted to engage in transverse grooves 23 formed in the lower surface of tube 16 and forming the teeth of a rack, whereby when actuating lever 21 is closed towards handle 2, pawl 22 engages in a groove 23 so as to move tube 16 forwards, i.e. to the left as shown in the drawing. A holding pawl 24 is mounted in body member 1 rearwardly of actuating lever 21 to engage with a groove 23 in tube 16 to hold the tube in a fixed position when actuating lever 1 is allowed to return to its forward position under the action of a return spring 25. Thus, in operation, actuating lever 21 is reciprocated by the user of the syringe so that tube 16 advances through the body member 1 and, in engagement with piston 12, forces material contained in the barrel through nozzle 9 into a delivery tube 11. The apparatus is so constructed and arranged that when stop member 18 of tube 16 abuts the rear face of body member 1, piston 12 has reached the end of its possible travel within barrel 3.

The rear part of tube 16 is provided with a downwardly facing cutout portion 26 so that when, as described above, tube 16 has reached the limit of its travel, pawl 22 engages with grooves formed in the lower surface of actuating rod 20. In order to assist in engagement of pawl 22 with the grooves formed in the lower face of rod 20, the latter is urged downwardly towards the bottom of tube 16 by means of a leaf spring 27.

As a result, further actuation of actuating lever 21 will force actuating rod 20 forwards and, with it, displacement bar 19 so as to pierce the weakened portion of piston 12 and, to this end, actuating rod 20 is conveniently provided with a tapered or pointed head 28. Once displacement bar 19 has pierced piston 12, it then passes, with continued operation of operating lever 19, through nozzle 9 and into a delivery tube attached thereto, thereby to displace remaining material from the nozzle and delivery tube.

When the operation is complete, the disposable elements of the syringe, namely the barrel, piston, end cap, delivery tube, and displacement bar may be removed from the body member and suitably disposed of. In order to return the piston actuating assembly to its initial position, i.e. the position as shown in FIG. 1 of the drawings, the tube and actuating rod are rotated so that pawls 22 and 24 no longer engage with the grooves therein and they are then manually pulled back to the position shown in FIG. 1.

Figure 3:
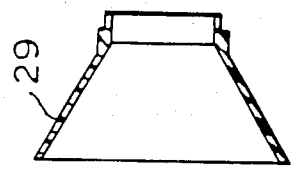
FIG. 3 is a longitudinal section through a funnel for use in filling the barrel of the syringe shown in FIG. 1.

In order to assemble a syringe assembly as shown in FIG. 1, a fresh displacement bar 19 is inserted into tube 16 so that its end abuts the end of actuating rod 20 and a fresh barrel member 3 provided with end cap 6 and piston 12 is engaged with body member 1. Before doing this, barrel member should first be filled with the material to be dispensed and this is suitably achieved by pouring the material to be dispensed into the barrel member, with piston 12 in position and without end cap 6 fitted, via disposable funnel 29, see FIG. 3 of the drawings. When the barrel has been filled with the material to be dispensed, end cap 6 is fitted followed by the delivery tube and, to assist in this operation, funnel 29 may be inverted to act as a support or stand for barrel 3.

As noted above, in the syringe shown in FIG. 1 the barrel piston, end cap, delivery tube, and displacement bar are all disposable, that is they are disposed of after use and not reused. Suitably, all these components may be made of sterilizable plastics materials and may be supplied to the user in a pre-sterilized form in a suitable sterilized package. The remainder of the components of the syringe are reusable and may be constructed of appropriate materials and are preferably formed of heat sterilizable materials, suitably of metal or heat sterilizable plastics.

In the syringe particularly described above, the displacement bar is a disposable item. In accordance with another embodiment of the invention, the actuating rod and displacement bars are formed integrally so that the displacement bar is not disposable. In this case, the displacement bar/actuating rod assembly may simply take the form of an elongate rod formed, in principle, by joining the abutting ends of the displacement bar and the actuating rod.

The illustrated structure may be modified, if desired, by forming the displacement bar and actuating rod integrally, and making the assembly somewhat shorter than the combined assembly shown in FIG. 1 so as to be substantially wholly contained within the tube 16. In this arrangement, the piston tube 16 is provided with two cut-outs: one, at the rear of the tube, is so positioned that when stop 18 abuts body 1, fixed pawl 22 is able to pass through it. The cut-out is sufficiently wide to allow tube 16 to be turned about its axis to disengage the driving pawl 20: a longitudinally extending slot connects this cut-out and is so positioned that when the piston head 17 abuts the body, when the tube is drawn to the rear, then tube 16 may be turned about its axis to re-engage pawl 20. The fixed pawl 22 is of a width capable of fitting within the interconnecting slot. When pawl 22 passes through the rearward slot, it engages with an annular groove in the displacement bar: turning the tube disengages the lever pawl 20 and allows the tube to be drawn to its starting position and re-engage with the lever pawl 20. The fixed pawl 22 maintains the displacement bar in its position, and by means of a spring loaded detent in the bar, the bar engages with the front of tube 16 after it has been withdrawn. Forward movement of the tube by means of the lever 21 allows the displacement bar to rupture the piston 12 and to pass forward into the delivery tube, thus displacing the material therein.

It is claimed:

1. A syringe comprising a body member detachably secured onto one end of a syringe barrel provided at its other end with a conical end cap terminating in a delivery tube and said barrel containing a piston member movable longitudinally therein, said piston member having a yieldable pressure face substantially complementary to the interior of said cap; a piston actuating assembly movably mounted in the body member and comprising an actuating tube generally coaxial with the barrel and a rod movably mounted within the actuating tube, said actuating tube having a longitudinal opening and said rod in said actuating tube having rack means thereon engageable by a pawl on a pivoted lever movable through said longitudinal opening to engage said rack means on said rod and thereby move a secondary plunger head after the piston member has moved to the distal end of said barrel, said pawl actuates said piston member and secondary plunger head in sequence to effect substantially complete discharge of the contents of the syringe barrel and a handle extending laterally from said body member and having a pivot supporting said pivoted lever whereby the said piston member is first displaced toward the distal end of the barrel to discharge a major portion of the contents of the barrel through said end cap and the said rod has said secondary plunger head thereon movable through the yieldable pressure face of said piston member and into the delivery tube of said end cap.

2. The syringe according to claim 1 in which said yieldable pressure face of said piston member is a truncated conical web having a central opening substantially complementary to the diameter of said second plunger and through which said secondary plunger is movable incident to discharging material contained within said conical web of said piston member.

3. The syringe according to claim 1 in which said conical end cap is detachably secured to said distal end of said barrel by thread means, whereby said barrel may be filled with material through said distal end thereof when said end cap is removed, and said syringe further including filling means for said barrel comprising a conical funnel having a discharge end complementary in size to the distal end of said barrel and interfitting the same for filling the barrel with material to be discharged therefrom.

* * * * *